United States Patent [19]

Schneider

[11] 4,331,667

[45] May 25, 1982

[54] QUINAZOLINES FOR CONTROLLING ECTOPARASITES

[75] Inventor: Rupert Schneider, Riehen, Switzerland

[73] Assignee: Sandoz Ltd., Basel, Switzerland

[21] Appl. No.: 231,001

[22] Filed: Feb. 4, 1981

[30] Foreign Application Priority Data

Feb. 8, 1980 [GB] United Kingdom ............... 8004276

[51] Int. Cl.³ .......................................... A61K 31/505
[52] U.S. Cl. ................................................. 424/251
[58] Field of Search ....................... 544/293; 424/251

[56] References Cited

U.S. PATENT DOCUMENTS 3,541,094 11/1970 Lutz et al. ........................ 544/293

OTHER PUBLICATIONS

Article–Les Organismes Auxiliaires en Verger de Pommiers (1974) p. 232.

Translation of Japanese Patent No. 103484/78, Inventor Miki (33 pages).
Martin et al., Pesticide Manual, 5th Ed., (1977), pp. 149, 161 & 326.
Barnett, FAO Agriculture Studies, No. 54 (1975), pp. 67-70.
Hall, J. of Economic Entomology, vol. 72, No. 3, pp. 441-446.
Jeppson et al., Mites Injurious to Economic Plants, (1975), p. 6.
Lutz et al., Chem. Abst., vol. 71 (1969), p. 30492v.
Miki, Chem. Abst., vol. 90 (1979), p. 87501u.

*Primary Examiner*—Sam Rosen
*Attorney, Agent, or Firm*—Gerald D. Sharkin; Richard E. Vila

[57] ABSTRACT

Disclosed is a method of controlling ectoparasites of the order Acari in animal livestock which comprises applying to the animal an effective amount of a 4-alkylaminoquinazoline, e.g. 4(n-$C_9H_{19}$NH)quinazoline or 4-(n-$C_{10}H_{21}$NH)quinazoline.

10 Claims, No Drawings

QUINAZOLINES FOR CONTROLLING ECTOPARASITES

The present invention relates to the combatting of certain ectoparasites of considerable economic significance.

In the rearing of animal livestock such as cattle and sheep, ectoparasites such as the tick cause enormous losses particularly as disease vectors.

Accordingly, the present invention provides a method of preventing and/or combatting ectoparasites of the order Acari in animal livestock which comprises topically applying to the animal an effective amount of a compound of formula I,

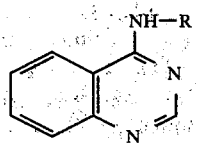

wherein
R is $C_{8-11}$ alkyl.
R may be branched or unbranched, and is preferably $C_{9-10}$ alkyl.
R is preferably unbranched.

4-Alkylamino-quinazolines as well as their fungicidal and acaricidal use are known i.a. from the DOS No. 1,642,333. Several compounds of formula I in salt form are specifically disclosed in this DOS. It has now surprisingly been found that the compounds of formula I are useful in preventing and/or combatting ectoparasites of the order Acari, especially against ticks.

These unexpected properties of the compounds of formula I are of considerable significance since there are rather few pesticides that can effectively be used against ectoparasites.

The control of ectoparasites is indeed very problematic, since numerous strains of ticks have developed resistance to a wide range of pesticides such as arsenic, hexachlorohexane, camphechlor, DDT, pyrethrines, carbamates and phosphorous compounds, having various primary sites of attack in the ectoparasite. It is therefore generally accepted, that it is highly desirable to develop active substitutes for the pesticides actually used for ectoparasite control, and particularly to develop substitutes which are chemically completely different from the compounds used hitherto for that purpose.

It has now surprisingly been found that the compounds of formula I are useful in controlling ectoparasites of the order Acari. Compounds belonging to the class of aminoquinazolines have hitherto not been suggested for use in control of ectoparasites.

Moreover, compounds structurally very closely related to compounds of formula I, e.g. the compound 4-(n-$C_{12}H_{25}$NH)-quinazoline, show despite significant acaricidal activity only a weak effect in the tests executed for evaluation of activity against ectoparasites of the order of Acari, whereas the compounds of formula I, especially the compounds of formula I wherein R is $C_9$- or $C_{10}$alkyl, particularly wherein R is n-$C_9$-$H_{19}$ or n-$C_{10}H_{21}$ are particularly effective in the method of the invention.

The compounds of formula I are applied to the ectoparasites of the order Acari, in free base form or in agriculturally acceptable acid addition salt form e.g. as hydrochloride or acetate, by topical treatment of the animals, e.g. by dusting, by dipping or by spray treatments with dilute aqueous form. The compounds of formula I are preferably used in free base form. The degree of dilution may vary although preferably a concentration in the range of 0.01 to 5.0%, particularly of 0.02 to 0.1%, by weight of the active agent is employed. The treatment is preferably repeated at intervals of between 7 to 21 days.

The active agent is conveniently formulated as a dust, dust concentrate, wettable powder, emulsifiable concentrate or as a solution, with conventional solid or liquid adjuvants. Particularly preferred compositions of the invention are liquid concentrates, especially those containing preferably 3.0 to 50% by weight of active agent, to be diluted with water before use. Such liquid concentrate preferably includes an emulsifying agent such as a polyglycolether derived from a high molecular weight alcohol, mercaptan or alkyl phenol with a alkylene oxide as well as a diluent such as a liquid aromatic hydrocarbon or mineral oil.

The ectoparasites of the order Acari against which the compounds of formula I have been found to be particularly effective are of the family Ixodidae e.g. the cattle ticks such as Boophilus spp e.g. *Boophilus microplus, Boophilus decoloratus* and *Boophilus annulatus;* Rhipicephalus spp such as *Rhipicephalus sanguineus, Rhipicephalus appendiculatus, Rhipicephalus pulchellus* and *Rhipicephalus evertsi;* Hyalomma spp such as *Hyalomma truncatum, Hyalomma rufipes, Hyalomma detritum, Hyalomma marginatum, Hyalomma dromedarii* and *Hyalomma anatolicum excavatum;* Amblyomma spp such as *Amblyomma variegatum, Amblyomma herbraeum, Amblyomma pomposum, Amblyomma americanum, Amblyomma cayennenese, Amblyomma maculatum, Amblyomma gemma* and *Amblyomma lepidium;* of the family Argasidae, e.g. Otobius spp such as *Otobius megnini* and Ornithodoros spp such as *Ornithodoros savignyi, Ornithodoros lahorensis* and *Ornithodoros tholozani;* of the family Psoroptidae e.g. *Psoroptes ovis* and *Psoroptes equi;* and of the family Sarcoptidae e.g. *Sarcoptes bovis* or *Sarcoptes scabici.*

The invention is illustrated by the following.

Test

Female fertilized adults (completely sucked with blood) of *Boophilus microplus* Biarra (organophosphorester-resistant strain) and *Boophilus microplus* Mt Alford (organophosphorester-resistant strain) are dipped into test solutions of 0.2 and 0.05% of 4-(n-$C_{10}H_{21}$NH) quinazoline by weight in water during 5 minutes. The ticks were dried in a sieve and then, for 30 seconds, upon a filterpaper.

The ticks were kept separate in glass tubes closed with gauze at 27° and 90% relative humidity. The observations made are set out in the following table.

| Concentration % | 0.2 | | 0.05 | |
| --- | --- | --- | --- | --- |
| Ticks | Bi(1) | Al(2) | Bi | Al |
| dead ticks before begin of oviposition (six days after treatment; % mortality) | 92 | 70 | 55 | 55 |
| time until oviposition begins (in days) | 2.0 | 2.4 | 2.6 | 2.3 |
| time until larvae emerged (in days) | — | — | 28 | 28 |

-continued

| Concentration % | 0.2 | | 0.05 | |
|---|---|---|---|---|
| Ticks | Bi$_{(1)}$ | Al$_{(2)}$ | Bi | Al |
| suppression of capacity of reproduction (% compared with control) | 100 | 100 | 92 | 89 |

$_{(1)}$Bi = Boophilus microplus Biarra
$_{(2)}$Al = Boophilus microplus Mt Alford Analogous results are obtained with 4-(n-C$_9$H$_{19}$NH) quinazoline
4-(n-C$_{11}$H$_{23}$NH) quinazoline The best results are obtained with the compounds of formula I in base form.

EXAMPLE

A herd of cattle severely infested with the cattle tick Boophilus microplus are sprayed at 21 day periods with a 0.05% by weight aqueous solution of 4-(n-C$_9$H$_{19}$NH)quinazoline. The spraying is effected on the cattle individually by means of a spray race. The cattle enter and leave the spray race through stoutly built races, the spray being applied at a pressure of 1.4 kg/cm$_2$ delivering 810 liters of wash per minute. The spray race is so designed that the whole skin surface of each animal is completely and thoroughly treated. The treatment is found to significantly reduce the tick infestation over the period of the treatment.

Analogous results are obtained with 0.05% by weight aqueous solutions of 4-(n-C$_{10}$H$_{21}$NH)quinazoline.

What is claimed is:

1. A method of preventing or combatting ectoparasites of the order Acari in animal livestock which comprises topically applying to the host animal an effective amount of a compound of formula I, $$\text{quinazoline with NH-R substituent}$$ I wherein R is C$_{8-11}$alkyl.

2. A method according to claim 1, wherein R is C$_9$-or C$_{10}$ alkyl.

3. A method according to claim 2, wherein R is straight chained.

4. A method according to claim 3, wherein the ectoparasites are of the families Ixodidae, Argasidae, Psoroptidae or Sarcoptidae in animal livestock.

5. A method according to claim 4, wherein the ectoparasites are Boophilus spp, Rhipicephalus spp, Hyalomma spp, Amblyomma spp, Otobius spp or Ornithodoros spp.

6. A method according to claim 3, wherein the compound of formula I is applied from a dilute aqueous solution by spraying or dipping the animal.

7. A method according to claim 6, wherein the active agent is applied as a 0.01 to 5.0% by weight aqueous solution.

8. A method according to claim 6 wherein the active agent is applied as a 0.02 to 0.1% by weight aqueous solution.

9. A method according to claim 6 wherein the compound of formula I is in base form.

10. A method according to claim 6 for the treatment of cattle or sheep.

* * * * *